United States Patent
Behnke, II et al.

(10) Patent No.: US 9,522,039 B2
(45) Date of Patent: *Dec. 20, 2016

(54) CREST FACTOR ENHANCEMENT IN ELECTROSURGICAL GENERATORS

(71) Applicant: Covidien LP, Mansfield, MA (US)

(72) Inventors: Robert J. Behnke, II, Erie, CO (US); Robert H. Wham, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 659 days.

This patent is subject to a terminal disclaimer.

(21) Appl. No.: 13/787,376

(22) Filed: Mar. 6, 2013

(65) Prior Publication Data
US 2013/0184699 A1    Jul. 18, 2013

Related U.S. Application Data

(63) Continuation of application No. 12/401,981, filed on Mar. 11, 2009, now Pat. No. 8,409,186.

(51) Int. Cl.
*A61B 18/18* (2006.01)
*A61B 18/04* (2006.01)
(Continued)

(52) U.S. Cl.
CPC .......... *A61B 18/18* (2013.01); *A61B 18/1206* (2013.01); *A61B 2018/00589* (2013.01);
(Continued)

(58) Field of Classification Search
CPC ................ A61B 18/1206; A61B 18/18; A61B 2018/00892; A61B 2018/00875; A61B 2018/00726; A61B 2018/00642; A61B 2018/00666; A61B 2018/1286; A61B 2018/00791; A61B 2018/00827; A61B 2018/00589; A61B 2018/00702
(Continued)

(56) References Cited

U.S. PATENT DOCUMENTS 3,436,563 A    4/1969 Regitz
3,963,030 A    6/1976 Newton
(Continued)

FOREIGN PATENT DOCUMENTS

DE    179607    3/1905
DE    1099658    2/1961
(Continued)

OTHER PUBLICATIONS

International Search Report EP09003678.2 dated Aug. 7, 2009.
(Continued)

*Primary Examiner* — Bhisma Mehta
*Assistant Examiner* — Bradley G Thomas, Jr.

(57) ABSTRACT

The present disclosure relates to an electrosurgical generator which includes a controller configured to generate a first pulse train having at least one first control pulse and at least one first reset pulse. The controller also includes a second pulse train having at least one second control pulse and at least one second reset pulse. The first control pulse(s) and the second control pulse(s) are asynchronous and the reset pulse(s) are synchronous. The electrosurgical generator also includes an RF output stage which includes a first switching element and a second switching element. The control pulses are configured to activate the first switching element and second switching elements, respectively, in an asynchronous fashion to generate a non-continuous RF waveform.

19 Claims, 7 Drawing Sheets

(51) Int. Cl.
*A61B 18/12* (2006.01)
*A61B 18/00* (2006.01)

(52) U.S. Cl.
CPC .............. *A61B 2018/00642* (2013.01); *A61B 2018/00666* (2013.01); *A61B 2018/00702* (2013.01); *A61B 2018/00726* (2013.01); *A61B 2018/00791* (2013.01); *A61B 2018/00827* (2013.01); *A61B 2018/00875* (2013.01); *A61B 2018/00892* (2013.01); *A61B 2018/1286* (2013.01); *A61B 2018/1823* (2013.01)

(58) Field of Classification Search
USPC ................................................ 606/32–34, 38
See application file for complete search history.

(56) References Cited

U.S. PATENT DOCUMENTS

| | | | |
|---|---|---|---|
| 4,191,188 A | 3/1980 | Belt et al. | |
| 4,429,694 A | 2/1984 | McGreevy | |
| 4,438,766 A | 3/1984 | Bowers | |
| 4,472,661 A | 9/1984 | Culver | |
| 4,767,999 A | 8/1988 | VerPlanck | |
| 4,788,634 A | 11/1988 | Schlecht et al. | |
| 5,318,563 A | 6/1994 | Malis et al. | |
| 5,370,645 A | 12/1994 | Klicek et al. | |
| 5,452,725 A | 9/1995 | Martenson | |
| 6,090,106 A * | 7/2000 | Goble ................ | A61B 18/1206 606/41 |
| 6,306,134 B1 | 10/2001 | Goble et al. | |
| 6,843,789 B2 | 1/2005 | Goble | |
| 6,939,347 B2 | 9/2005 | Thompson | |
| 6,942,660 B2 | 9/2005 | Pantera et al. | |
| 7,513,896 B2 * | 4/2009 | Orszulak ............... | A61B 18/12 606/32 |
| 8,152,802 B2 | 4/2012 | Podhajsky et al. | |
| 8,162,932 B2 | 4/2012 | Podhajsky et al. | |
| 8,167,875 B2 | 5/2012 | Podhajsky et al. | |
| 8,174,267 B2 | 5/2012 | Brannan et al. | |
| 8,180,433 B2 | 5/2012 | Brannan et al. | |
| 8,211,100 B2 | 7/2012 | Podhajsky et al. | |
| 8,226,639 B2 | 7/2012 | Podhajsky et al. | |
| 8,242,782 B2 | 8/2012 | Brannan et al. | |
| 8,248,075 B2 | 8/2012 | Brannan et al. | |
| 8,257,349 B2 | 9/2012 | Orszulak | |
| 8,287,527 B2 | 10/2012 | Brannan et al. | |
| 8,287,528 B2 | 10/2012 | Wham et al. | |
| 8,287,529 B2 | 10/2012 | Orszulak | |
| 8,333,759 B2 | 12/2012 | Podhajsky | |
| 8,346,370 B2 | 1/2013 | Haley et al. | |
| 8,377,053 B2 | 2/2013 | Orszulak | |
| 8,403,924 B2 | 3/2013 | Behnke et al. | |
| 8,409,186 B2 | 4/2013 | Behnke et al. | |
| 2002/0052599 A1 | 5/2002 | Goble | |
| 2005/0004564 A1 | 1/2005 | Wham et al. | |
| 2006/0161148 A1 * | 7/2006 | Behnke ............... | A61B 18/1206 606/34 |
| 2006/0178667 A1 | 8/2006 | Sartor et al. | |
| 2008/0015564 A1 | 1/2008 | Wham et al. | |
| 2009/0069801 A1 | 3/2009 | Jensen et al. | |
| 2010/0094271 A1 | 4/2010 | Ward et al. | |
| 2010/0094288 A1 | 4/2010 | Kerr | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 880220 | 6/2006 |
| EP | 1 681 026 A2 | 7/2006 |
| EP | 1681026 | 7/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2 154 881 A | 9/1985 |
| GB | 2154881 | 9/1985 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO 02/32335 | 4/2002 |
| WO | WO 2008/003058 | 1/2008 |

OTHER PUBLICATIONS

Wald et al., "Accidental Burns", JAMA, Aug. 18, 1971, vol. 217, No. 7, pp. 916-921.

Vallfors et al., "Automatically Controlled Bipolar Electrosoagulation—'COA-COMP'" Neurosurgical Review 7:2-3 (1984) pp. 187-190.

Sugita et al., "Bipolar Coagulator with Automatic Thermocontrol" J. Neurosurg., vol. 41, Dec. 1944, pp. 777-779.

Muller et al. "Extended Left Hemicolectomy Using the LigaSure Vessel Sealing System" Innovations That Work; Company Newsletter; Sep. 1999.

Ogden Goertzel Alternative to the Fourier Transform: Jun. 1993 pp. 485-487 Electronics World; Reed Business Publishing, Sutton, Surrey, BG vol. 99, No. 9. 1687.

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

Richard Wolf Medical Instruments Corp. Brochure, "Kleppinger Bipolar Forceps & Bipolar Generator" 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

(56) References Cited

OTHER PUBLICATIONS

Geddes et al., "The Measurement of Physiologic Events by Electrical Impedence" Am. J. Ml, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg el al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014158.3 dated Dec. 28, 2005.
International Search Report EP 05021944.3 dated Jan. 18, 2006.
International Search Report EP 05022350.2 dated Jan. 18, 2008.
International Search Report EP 06000708.5 dated Apr. 21, 2006.
International Search Report—extended EP 06000708.5 dated Aug. 22, 2008.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 18, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
Supplementary European Search Report dated Nov. 29. 2011 for EP Appln. No. EP 09 76 3515.
The extended European Search Report, corresponding to European Application No. 13 17 8170.0, dated Dec. 6, 2013; 6 pages.

* cited by examiner

CREST FACTOR ENHANCEMENT IN ELECTROSURGICAL GENERATORS

CROSS-REFERENCE TO RELATED APPLICATIONS

The present application is a continuation application which claims the benefit of and priority to U.S. patent application Ser. No. 12/401,981, filed Mar. 11, 2009, the entire contents of which are incorporated by reference herein.

BACKGROUND

Technical Field

The present disclosure relates to electrosurgical apparatuses, systems and methods. More particularly, the present disclosure is directed to enhancing and/or maintaining a crest factor of a radiofrequency (RF) waveform in electrosurgical generators.

Background of Related Art

Energy-based tissue treatment is well known in the art. Various types of energy (e.g., electrical, ultrasonic, microwave, cryo, heat, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is most commonly a monopolar procedure that is particularly useful in the field of cancer treatment, where one or more RF ablation needle electrodes (usually of elongated cylindrical geometry) are inserted into a living body. A typical form of such needle electrodes incorporates an insulated sheath from which an exposed (uninsulated) tip extends. When RF energy is provided between the return electrode and the inserted ablation electrode, RF current flows from the needle electrode through the body. Typically, the current density is very high near the tip of the needle electrode, which tends to heat and destroy surrounding issue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

It is known in the art that the crest factor of a waveform is a useful measure of the coagulating ability of a radio frequency output. Thus, maintaining a high crest factor would be beneficial in electrosurgical procedures.

SUMMARY

The present disclosure relates to an electrosurgical generator which includes a controller configured to generate a first pulse train having at least one first control pulse and at least one first reset pulse. The controller also includes a second pulse train having at least one second control pulse and at least one second reset pulse. The first and second control pulses are asynchronous and the reset pulses are synchronous. The electrosurgical generator also includes an RF output stage which includes a first switching element and a second switching element. The first control pulse and the second control pulse are configured to activate the first switching element and second switching element, asynchronously, to generate a non-continuous RF waveform. Also, the first reset pulse and the second reset pulse are configured to synchronously activate the first and second switching elements, respectively, to reset the RF output stage.

A method for performing electrosurgery includes the step of generating a first pulse train, which includes a first control pulse and a first reset pulse. The method also includes the step of generating a second pulse train, which includes a second control pulse and a second reset pulse. The first and second control pulses are asynchronous and the first and second reset pulses are synchronous. A further step includes supplying the first and second control pulse trains to an RF output stage having a first switching element and a second switching element. The method also includes the step of activating the first and second switching elements asynchronously to generate a non-continuous RF waveform in response to the asynchronous first and second control pulses. The method may further include the step of activating first and second switching elements synchronously to reset the RF output stage in response to the at least one first reset pulse and at least one second reset pulse.

Another embodiment of the present disclosure includes a method for performing electrosurgery which includes the steps of: setting a desired crest factor for a non-continuous RF waveform; determining an actual crest factor of a non-continuous RF waveform, comparing the desired crest factor with the actual crest factor, and performing an adjustment of a property of a first reset pulse and a property of a second reset pulse to maintain a desired crest factor. The controller is configured to generate a first pulse train having a first control pulse and a first reset pulse. The controller is also configured to generate a second pulse train, having a second control and second reset pulse. The first and second control pulses are asynchronous and the first and second reset pulses are synchronous. Also, the method includes the step of comparing the desired crest factor with the actual crest factor.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The electrosurgical generator, according to the present disclosure, can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
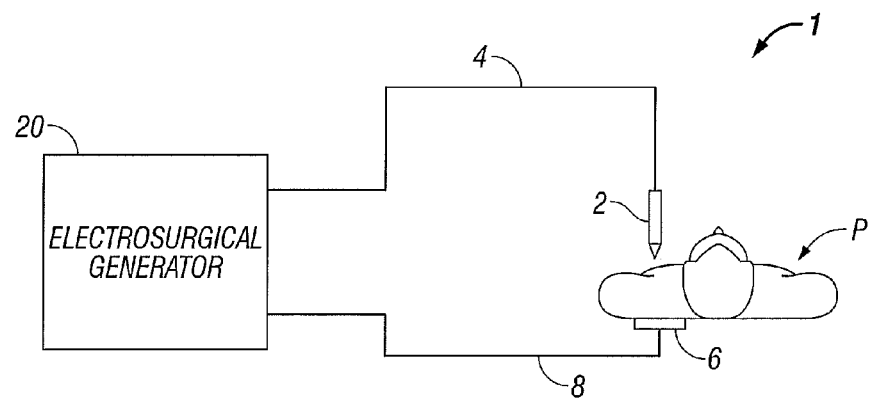
FIGS. 1A-1B are schematic block diagrams of an electrosurgical system according to the present disclosure.

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via an supply line 4, which is connected to an active terminal 30 (FIG. 2) of the generator 20, allowing the instrument 2 to coagulate, seal, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, respectively, which are disposed at the ends of the supply line 4 and the return line 8.

The system 1 may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Figure 1B:
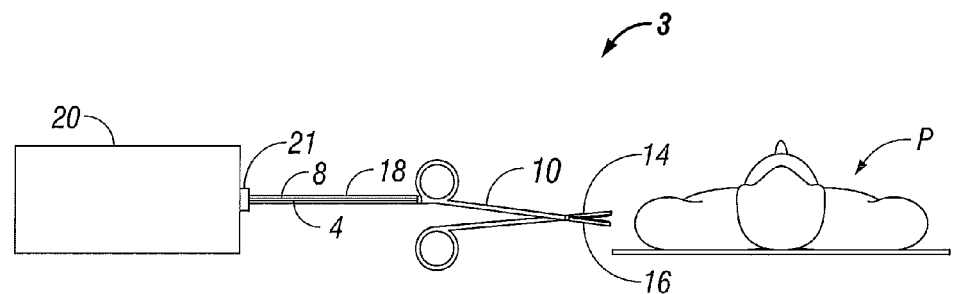
Figure 2:
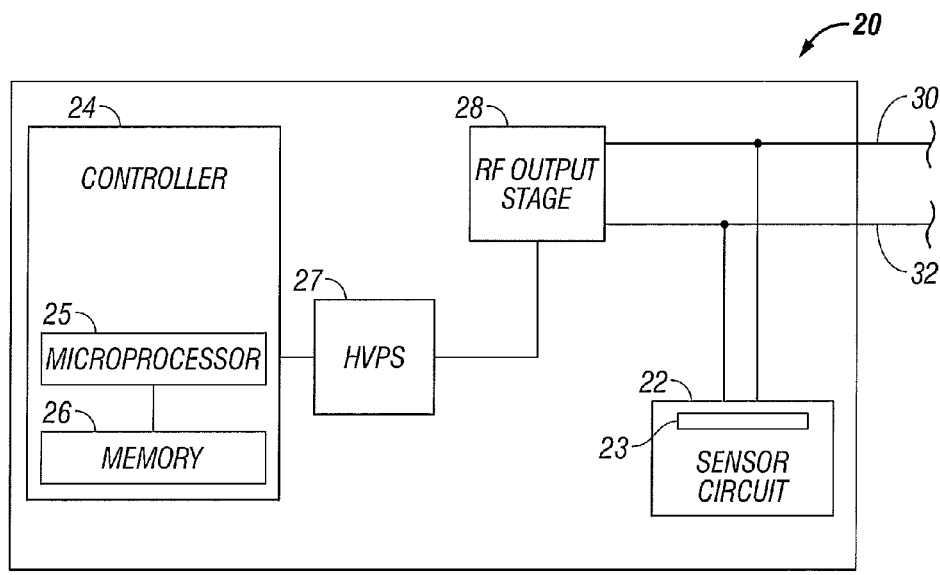
FIG. 2 is a schematic block diagram of a generator according to one embodiment of the present disclosure.

FIG. 1B is a schematic illustration of a bipolar electrosurgical system 3 according to the present disclosure. The system 3 includes a bipolar electrosurgical forceps 10 having one or more electrodes for treating tissue of a patient P. The electrosurgical forceps 10 includes opposing jaw members having an active electrode 14 and a return electrode 16 disposed therein. The active electrode 14 and the return electrode 16 are connected to the generator 20 through cable 18, which includes the supply and return lines 4, 8 coupled to the active and return terminals 30, 32, respectively (FIG. 2). The electrosurgical forceps 10 is coupled to the generator 20 at a connector 21 having connections to the active and return terminals 30 and 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

FIG. 2 illustrates a schematic block diagram of the generator 20 according to one embodiment of the present disclosure. The generator 20 includes a controller 24, a high voltage DC power supply 27 (HVPS) and an RF output stage 28. The controller 24 includes a power supply (not shown), for example, a low voltage DC power supply, which provides low voltage power to circuitry of the controller 24 and/or RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal 30. The energy is returned thereto via the return terminal 32.

In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The generator 20 may include a plurality of connectors to accommodate various types of electrosurgical instruments (e.g., instrument 2, electrosurgical forceps 10, etc.). Further, the generator 20 is configured to operate in a variety of modes such as ablation, monopolar and bipolar cutting coagulation, etc. It is envisioned that the generator 20 may include a switching mechanism (e.g., relays) to switch the supply of RF energy between the connectors, such that, for instance, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuit 22 and/or crest factor detection circuit 23, which both may include a plurality of sensors measuring a variety of tissue and energy properties (e.g., tissue impedance, tissue temperature, output current and/or voltage, crest factor, etc.), provide feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

Figure 3:
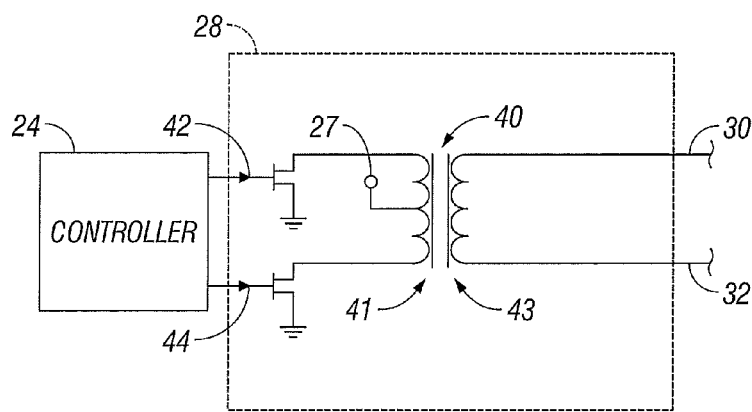
FIG. 3 is a schematic diagram of a non-single ended transformer according to the present disclosure.

FIG. 3 depicts a schematic diagram of the RF output stage 28 having a transformer 40. In one embodiment, transformer 40 is a non-single ended transformer, configured in a simplified push-pull topology. It is also envisioned the present system and method may be applied to any non-single ended transformer topology (e.g., full bridge) having a primary winding 41 and secondary winding 43. The primary winding 41 is coupled to the HVPS 27 and includes a first switching element 42 and a second switching element 44 which may be, for example, transistors, FETs, MOSFETs or the like. The switching elements 42 and 44 are coupled to the controller 24 which controls the operation thereof to generate RF energy. More specifically, the controller 24 is configured to transmit a low-voltage clock signal of a first pulse train 60 to switching element 42 and a second pulse train 62 to switching element 44 of the RF output stage 28 (shown in FIG. 6). The secondary winding 43 is coupled to the active terminal 30 and return terminal 32.

In various types of control loops it may be desirable to measure certain properties of RF energy being delivered by the RF output stage 28. In particular, voltage is continuously measured and impedance is calculated by the sensor circuit 22. In one embodiment, a control loop may be configured to measure the crest factor of a waveform and maintain the crest factor at a desired level. Crest factor is a useful measurement of the coagulation ability of an RF output waveform, thus increasing or controlling the crest factor is beneficial to electrosurgical procedures involving coagulation.

The present disclosure provides a system and method for maintaining a desired crest factor of an RF waveform. A high crest factor waveform is particularly helpful in electrosurgical procedures. The crest factor is defined as the ratio of the peak voltage and root mean square (RMS) voltage for symmetrical waveforms, those having a 100% duty cycle (e.g., when there is no interruption or pause in the RF waveform).

$$CF = V_{PEAK}/V_{RMS} \quad (1)$$

For non-symmetrical waveforms, the crest factor is defined as the ratio of peak to peak voltage and twice the RMS voltage.

$$CF = V_{(PEAK-PEAK)}/2 * V_{RMS} \quad (2)$$

Electrosurgical generators have difficulties generating high crest factor waveforms primarily due to excessive ringing, during the off-time or pause stage. The ringing in the RF waveform is especially excessive in high impedance loads. This occurs due to an increase in the RMS of the waveform and which decreases the crest factor, as seen in the above formula (2). When the undesired ringing is removed, the RMS of the waveform is decreased, thus increasing the crest factor (e.g., maintaining the crest factor).

Figure 4:
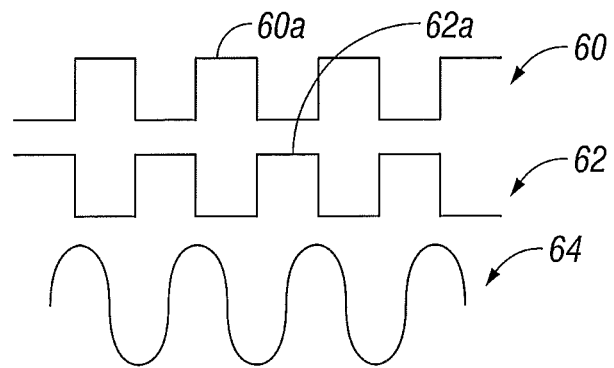
FIG. 4 is a schematic diagram of a plurality of pulse trains and a 100% duty cycle RF waveform output according to the present disclosure.

FIG. 4 illustrates a schematic diagram of a plurality of pulse trains and a corresponding 100% duty cycle RF waveform. As mentioned above, the controller 24 is configured to transmit a low-voltage clock signal sourced from the low-voltage power supply (not shown), as a first pulse train 60 to switching element 42 and a second pulse train 62 to switching element 44 of the RF output stage 28. Each of the pulse trains includes a plurality of control pulses 60a and 62a, respectively. When a 100% duty cycle waveform is desired, i.e., when there is no pause or interruption in power (shown in output wave 64 in FIG. 4), the first and second control pulse trains 60a and 62a are non-synchronous and continuous. The RF waveform 64 is generated as the first pulse train 60 and the second pulse train 62 to control the respective switching elements 40 and 42.

More specifically, the first pulse train 60 activates the pull of the RF output stage 28 when the square wave of the clock signal is at its highest amplitude, namely when the first control pulse 60a activates the switching element 42. The second pulse train 62 activates the push of the RF output stage 28 when the square wave of the clock signal is at its highest amplitude, such that the second control pulse 62a activates the switching element 44. By alternating the first and second control pulses 60a and 62a and spacing the control pulses 60a and 62a at ½ cycle timing (e.g., 180° out of phase), the RF waveform 64 is created at a specified frequency. Further, tuning can be done with inductors and capacitors and/or the parasitics of the transformer 40 to give a sinusoidal output as illustrated in output wave 64 in FIG. 4.

Figure 5:
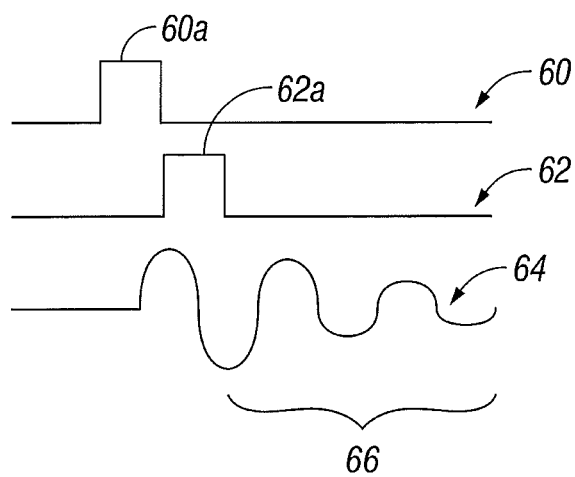
FIG. 5 is a schematic diagram of a plurality of pulse trains and a less than 100% duty cycle RF waveform output according to the present disclosure.

FIG. 5 depicts a schematic diagram of a plurality of pulse trains and a less than 100% duty cycle RF waveform output. The waveform 64 has a duty cycle of less than 100%. The first and second control pulses 60a and 62a are out of phase by 180°. In other words, the pulses are staggered, which allows for generation of non-synchronous waveforms. Further, there is a period of time when both the first and second control pulses 60a and 62a are paused to provide for off-time of the waveform. Ringing occurs in a region 66 when the first and second control pulse trains 60a and 62b are paused during the RF waveform off time, hence less than 100% duty cycle.

The region 66 shows the RF waveform 64 decaying steadily due to a pause in pulse trains 60 and 62, i.e., no activity. The region 66 is defined as the region where switching elements 42 and 44 (shown in FIG. 3) do not receive the pulse trains 60 and 62 from the controller 24. Although there is a pause in the pulse trains 60 and 62, there is still sufficient energy stored in the tuning elements of the transformer 40, thus energy rings out. When the control pulse trains 60 and 62 are stopped in the RF output stage 28, ringing occurs in the region 66 of the waveform 64, since stored energy still exists in the circuitry. The ringing in the region 66, in turn, reduces the crest factor in the RF waveform 64, as illustrated in FIG. 5. In order to maintain a high crest factor waveform output of the electrosurgical unit, the ringing in the waveform 64, shown in region 66 must be decreased and/or eliminated.

Figure 6:
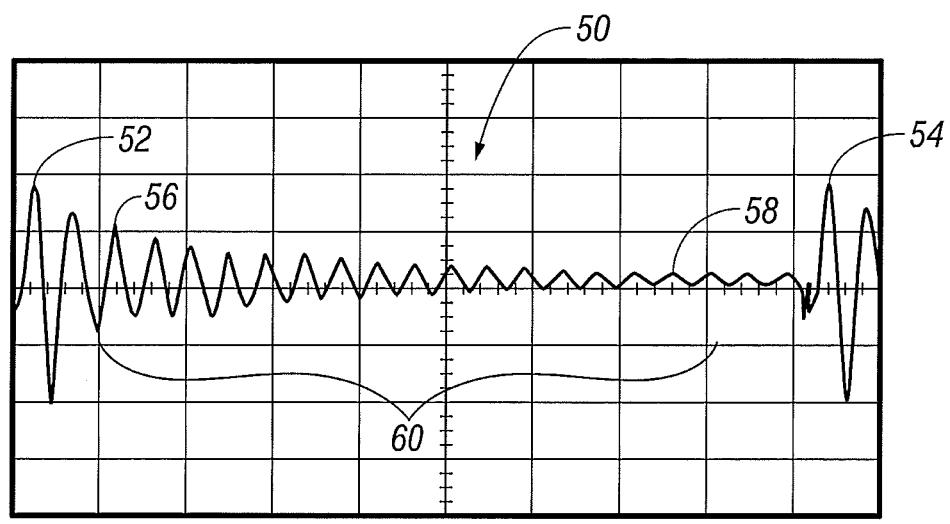
FIG. 6 is a graph of a low crest factor RF waveform showing desired and undesired waves according to the present disclosure.

FIG. 6 illustrates the effect of ringing on non-synchrounous waveforms with less than 100% duty cycle. FIG. 6 shows a graph of a low crest factor RF waveform 50 showing desired and undesired waves according to the present disclosure. The low crest factor waveform 50 includes desired waves 52 and 54 and an excessive ringing wave region 60. The excessive ringing propagates from an undesired wave 56 to a smaller undesired wave 58, with gradually decreasing sized waves. The RMS of the waveform 50 is increased due to excessive ringing, thus decreasing the crest factor.

Figure 7:
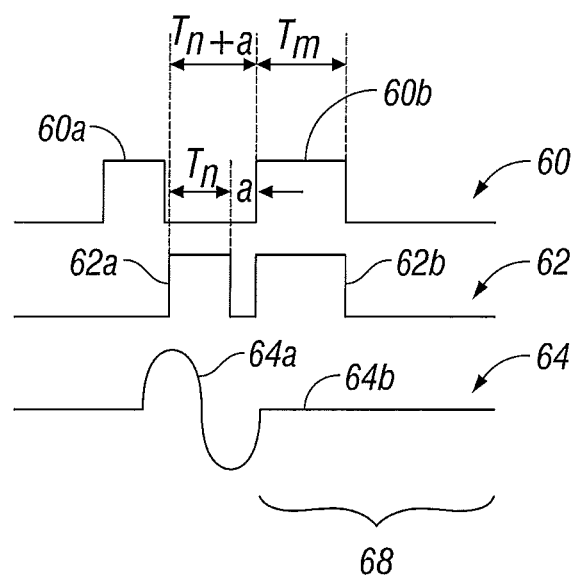
FIG. 7 is a schematic diagram of a plurality of pulse trains and reset pulses and a less than 100% duty cycle RF waveform output according to the present disclosure.

FIG. 7 depicts a schematic diagram of a plurality of pulse trains and reset pulses adapted to generate a less than 100% duty cycle RF waveform output, according to the present disclosure. To maintain a high crest factor, the first and second pulse trains 60 and 62 include, in addition to the first and second control pulse 60a and 62a, a first and second reset pulses 60b and 62b which are transmitted synchronously and simultaneously (e.g., in phase) to the switching elements 42 and 44. The reset pulses are preferably of substantially the same duration. When the first and second reset pulses 60b and 62b are synchronously and simultaneously transmitted by the controller 24, the non-continuous RF waveform 64 generates substantially no ringing. Namely, the controller 24 is short-circuiting the RF output stage at the switching elements 42 and 44 by transmitting first and second reset pulses 60b and 62b simultaneously. The substantial decrease in ringing is depicted at 64b of the waveform 64 in region 68 due to short-circuiting of the RF output stage 28.

It is envisioned that the timing of the first and second reset pulses 60b and 62b may be adjusted depending on the patient load and/or different electrosurgical procedure. For example, the start time of first and second reset pulse 60b and 62b transmitted by the controller 24 may vary. It is also envisioned that the duration of the first and second reset pulses 60b and 62b may vary in different electrosurgical procedures and/or different patients. All of these required and/or desired adjustments may be made by the controller 24 by transmitting the clock signal to the switching elements.

Figure 8:
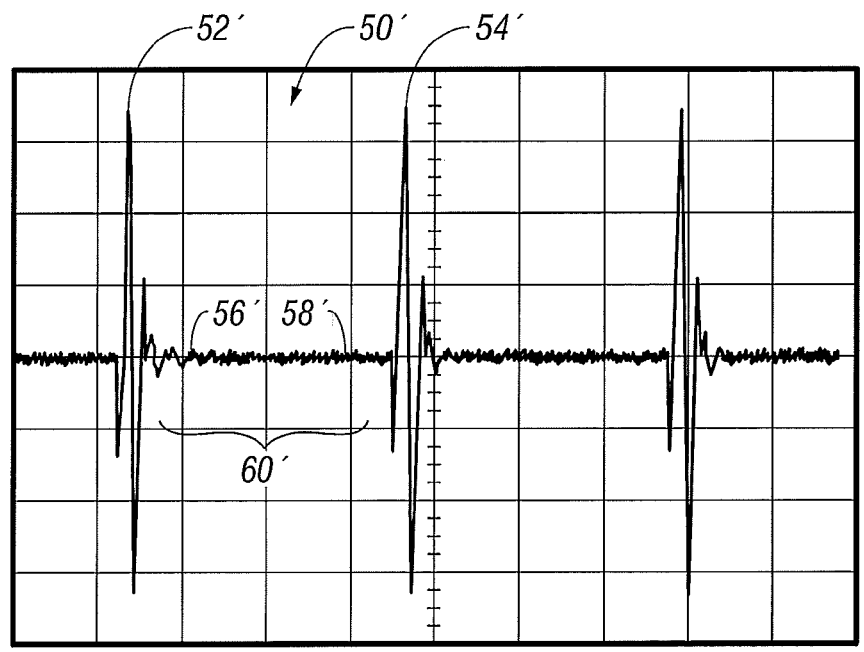
FIG. 8 is a graph of a high crest factor RF waveform showing desired and undesired waves according to the present disclosure.

FIG. 8 illustrates a graph of a high crest factor RF waveform 50' showing desired and undesired waves according to the present disclosure. The high crest factor waveform 50' includes desired waves 52' and 54'. The high crest factor waveform 50' also includes an excess ringing wave region 60'. The excessive ringing is reduced and propagates between undesired waves 56' and 58'. The reduction in the ringing is seen in the undesired waves 56', 58' being substantially similar in size. Unlike the excessive ringing wave region 60, the waves of region 60' are also substantially smaller. In this scenario, the RMS of the waveform 50' is decreased, since the undesired ringing waves 56' and 58' are small, thus increasing the crest factor.

Figure 9:
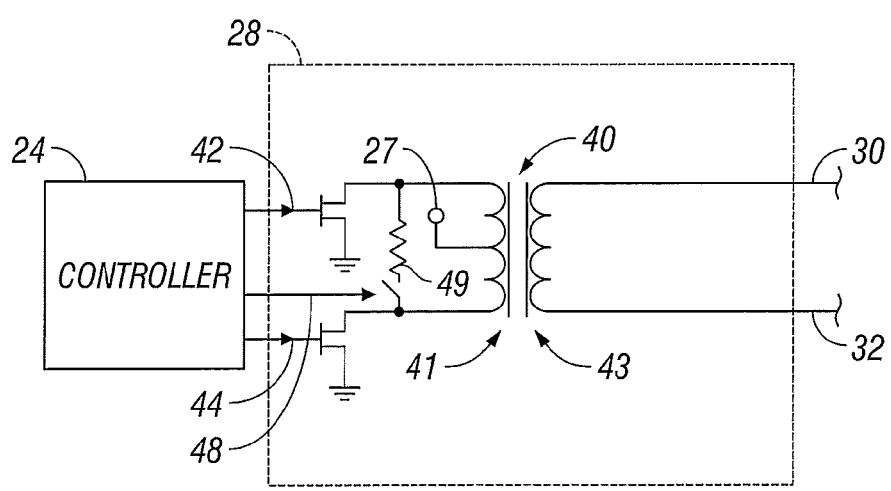
FIG. 9 is a schematic diagram of a non-single ended transformer according to another embodiment of the present disclosure.
Figure 10:
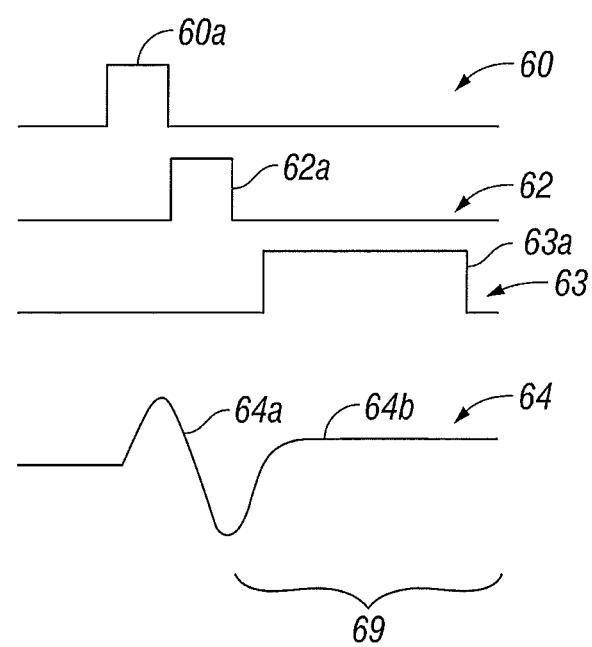
FIG. 10 is a schematic diagram of a plurality of pulse trains according to another embodiment of the present disclosure.

FIGS. 9 and 10 illustrate another embodiment of present disclosure. FIG. 9 is a schematic diagram of the RF output stage 28 according to another embodiment of the present disclosure. The RF output stage 28 includes a non-single ended transformer 40 configured in a simplified push-pull topology. Transformer 40 includes a switching element 42, a switching element 44 and a switching element 48. The switching element 48 is coupled in series to a resistive load 49. In addition to transmitting a clock frequency of a first pulse train 60 and a second pulse train 62 to the switching elements 42 and 44 of the RF output stage 27, respectively, the controller 24 also transmits a third pulse train 63 to the switching element 48.

FIG. 10 illustrates a schematic diagram of a plurality of pulse trains transmitted by the controller 24. The third control pulse lasts a period which is substantially for the duration of the off-time of the switching elements 42 and 44, such that during the off-time at switching elements 42 and 44, the switching element 48 is activated. As a result, the energy out of the transformer 40 and all of the inductors and capacitors and/or the parasitics of the transformer 40 is dumped into the resistive load 49. During the activation of the switching element 48, the RF waveform 64 shows substantially no ringing at region 69 since all the energy was dumped into the resistive load 49. The substantial decrease in ringing is depicted at 64b of the waveform 64 in region 69. Therefore, the crest factor of RF waveform 64 is maintained and/or increased, thus aiding in coagulation in electrosurgical procedures.

Figure 11:
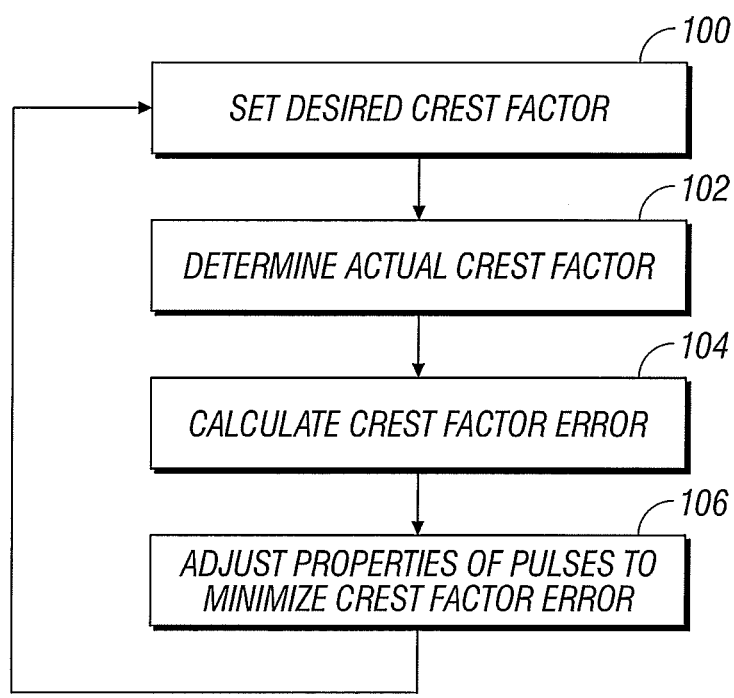
FIG. 11 is a flow chart of a method of maintaining a crest factor according to the present disclosure.

FIG. 11 shows a flow chart of a method for maintaining a desired crest factor according to the present disclosure. The method utilizes a crest factor detection circuit 23 which can be implemented in a closed loop control scheme as part of the sensor circuit 22. As mentioned above, to maintain the desired crest factor of the RF waveform 64, excessive ringing must be minimized. In step 100, a desired crest factor is selected and set on the generator 20. A user may manually set the desired crest factor on the generator 20 or the desired crest factor may be automatically set by the generator 20. It is envisioned that the automatic determination of the desired crest factor of generator 20 may depend on any other inputs entered by the user. The desired crest factor may be a value that is selected for a specific electrosurgical procedure and/or a value that is associated with a certain electrosurgical instrument.

In step 102, the crest factor detection circuit 23 calculates and determines an actual crest factor of the non-continuous RF waveform 64 (FIG. 7). The crest factor detection circuit 23 measures the voltage and calculates the peak and RMS voltage based on the above-discussed formulas (1) and (2). The voltage values are then used by the crest factor detection circuit 23 to determine the crest factor. In step 104, the microprocessor 25 and/or the crest factor detection circuit 23 compares the actual crest factor with the desired crest factor, thereby determining a crest factor error. The controller 24 determines if the actual crest factor is lower or higher than the desired crest factor. If the desired crest factor is less than or greater than the actual crest factor, the method proceeds to step 106, in which the properties of the first and second reset pulses 60b and 62b (FIG. 7) are adjusted by the controller 24 in order to decrease or increase the actual crest factor in order to match the desired crest factor. For example, frequency, period, duty cycle and other properties of the first and second reset pulses 60b and 62b may be adjusted.

According to one embodiment of the present disclosure, an activation time $T_n$+a (e.g., duty cycle) and a duration time $T_m$ (e.g., period of the pulse) of the synchronous reset pulses 60b and 62b may be varied. In particular, the duty cycle of the first and second reset pulses 60b and 62b transmitted by the controller 24 may be varied by adjusting the off-time period, $T_n$+a, wherein $T_n$ is the time period or remaining portion of the control pulse 62a, and wherein a is the time period between the trailing control pulse (e.g., control pulse 62a) and the first and second reset pulses 60b and 62b. As shown in FIG. 7, the on-time period, $T_m$, between the synchronous reset pulses 60b and 62b may also be adjusted. Some of the factors that may determine the variation of the activation time $T_n$+a and the duration time $T_m$ of the first and second reset pulses 60a and 60b are the tissue composition of the patient, the user's treatment plan, and/or the effect on certain parameters of the waveform (e.g., crest factor, wave length, wave period, etc.).

Afterwards, the method loops back to step 100 and repeats the steps of maintaining a desired crest factor. It is also envisioned that an additional step may be included to scan the actual RF waveform for ringing beyond the specified duty cycle. As a result of the scan, the RF waveform may be analyzed to determine when the following synchronous reset pulses and/or the control pulses may be activated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
   an RF output stage configured to generate a non-continuous RF waveform based on a desired crest factor;
   a controller configured to generate:
   a first pulse train including at least one first reset pulse; and
   a second pulse train including at least one second reset pulse, wherein the at least one first reset pulse and the at least one second reset pulse are synchronous; and
   a crest factor detection circuit configured to determine a crest factor of the non-continuous RF waveform and adjust at least one property of each of the first and second reset pulses based on the crest factor.

2. An electrosurgical generator according to claim 1, wherein the first pulse train includes at least one first control pulse, and the second pulse train includes at least one second control pulse.

3. An electrosurgical generator according to claim 2, wherein the at least one first reset pulse follows the at least one first control pulse and the at least one second reset pulse follows the at least one second control pulse.

4. An electrosurgical generator according to claim 2, wherein the at least one first control pulse and the at least one second control pulse are asynchronous.

5. An electrosurgical generator according to claim 2, wherein the RF output stage includes a first switching element and a second switching element, the at least one first control pulse and the at least one second control pulse are configured to activate the first and second switching elements asynchronously to generate a non-continuous RF waveform, and the at least one first reset pulse and the at least one second reset pulse are configured to synchronously activate the first and second switching elements, respectively, to reset the RF output stage.

6. An electrosurgical generator according to claim 5, wherein the RF output stage further includes a non-single ended transformer.

7. An electrosurgical generator according to claim 6, wherein the transformer is configured in a full-bridge topology.

8. An electrosurgical generator according to claim 6, wherein the transformer is configured in a push-pull topology.

9. An electrosurgical generator according to claim 6, wherein the transformer includes a primary winding and a secondary winding, the primary winding including the first and second switching elements.

10. An electrosurgical generator according to claim 9, wherein the primary winding further includes a third switching element coupled to a resistive load.

11. An electrosurgical generator according to claim 10, wherein the controller is configured to generate a third pulse train including a third control pulse, the third control pulse being configured to activate the third switching element during an off-time of the first and second switching elements to transfer remaining energy stored in the RF output stage to the resistive load.

12. An electrosurgical generator, comprising:
    a controller configured to generate a first control pulse including a first reset pulse and a second control pulse including a second reset pulse;
    an RF output stage configured to receive the first and the second control pulses and generate a non-continuous RF waveform; and
    a sensor circuit configured to determine an actual crest factor of the non-continuous RF waveform,
    wherein the controller is further configured to compare the actual crest factor to a desired crest factor, and adjust at least one property of the first reset pulse and at least one property of the second reset pulse to adjust the actual crest factor, the first reset pulse and the second reset pulse being configured to reset the RF output stage thereby maintaining the desired crest factor.

13. An electrosurgical generator according to claim 12, wherein the at least one property of each of the first and second reset pulses is a start time of the first and second reset pulses.

14. An electrosurgical generator according to claim 12, wherein the at least one property of each of the first and second reset pulses is a time duration of the activation of the first and second reset pulses.

15. An electrosurgical generator according to claim 12, wherein the controller is further configured to adjust at least one of the frequency, period, or duty cycle of the at least one first reset pulse.

16. An electrosurgical generator according to claim 12, wherein the controller is further configured to adjust at least one of the frequency, period and duty cycle of the at least one second reset pulse.

17. An electrosurgical generator according to claim 12, wherein the at least one property of the at least one first reset pulse and the at least one property of the at least one second reset pulse are the same.

18. An electrosurgical generator according to claim 12, wherein the desired crest factor is set automatically by the electrosurgical generator.

19. An electrosurgical generator according to claim 12, wherein the desired crest factor is set manually by a user.

* * * * *

UNITED STATES PATENT AND TRADEMARK OFFICE
CERTIFICATE OF CORRECTION

| | | |
|---|---|---|
| PATENT NO. | : 9,522,039 B2 | Page 1 of 1 |
| APPLICATION NO. | : 13/787376 | |
| DATED | : December 20, 2016 | |
| INVENTOR(S) | : Robert J. Behnke, II and Robert H. Wham | |

It is certified that error appears in the above-identified patent and that said Letters Patent is hereby corrected as shown below:

On the Title Page

Item (63), the Related U.S. Application Data should read as below:
Continuation of application No. 12/401,981 filed on Mar. 11, 2009, now Pat. No. 8,409,186, which claims benefit of 61/036,323 filed on Mar. 13, 2008.

Signed and Sealed this
Twenty-fifth Day of April, 2017

Michelle K. Lee
*Director of the United States Patent and Trademark Office*